United States Patent
Wang et al.

(10) Patent No.: US 9,637,781 B2
(45) Date of Patent: May 2, 2017

(54) MIRNA ANALYSIS METHODS

(71) Applicant: THE JOHNS HOPKINS UNIVERSITY, Baltimore, MD (US)

(72) Inventors: Tza-Huei Wang, Timonium, MD (US); Kelvin J. Liu, Baltimore, MD (US); Yunke Song, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 102 days.

(21) Appl. No.: 14/378,675

(22) PCT Filed: Feb. 13, 2013

(86) PCT No.: PCT/US2013/025860
§ 371 (c)(1),
(2) Date: Aug. 14, 2014

(87) PCT Pub. No.: WO2013/122996
PCT Pub. Date: Aug. 22, 2013

(65) Prior Publication Data
US 2015/0031573 A1    Jan. 29, 2015

Related U.S. Application Data

(60) Provisional application No. 61/598,513, filed on Feb. 14, 2012.

(51) Int. Cl.
*C12Q 1/68* (2006.01)
*C12P 19/34* (2006.01)
(Continued)

(52) U.S. Cl.
CPC .......... *C12Q 1/6862* (2013.01); *C12N 15/111* (2013.01); *C12Q 1/25* (2013.01);
(Continued)

(58) Field of Classification Search
CPC .. C12C 1/68; C12C 1/25; C07H 21/04; C12N 15/111; B01D 57/02; C40B 30/04
(Continued)

(56) References Cited

U.S. PATENT DOCUMENTS 8,278,035 B2 * 10/2012 Dawson ............... C12Q 1/6816
435/6.11
2006/0078925 A1    4/2006 Mourelatos et al.
(Continued)

FOREIGN PATENT DOCUMENTS

EP        1735459 B1    1/2012
WO    2008070675 A2    6/2008
(Continued)

OTHER PUBLICATIONS

Wang et al, Free Solution Hydrodynamic Separation of DNA Fragments from 75 to 106 000 Base Pairs in a Single Run, 2010 JACS, 132, 40-41.*
(Continued)

*Primary Examiner* — Narayan Bhat
(74) *Attorney, Agent, or Firm* — John Hopkins Technology Transfer

(57) ABSTRACT

The present invention provides a PCR-free, multiplexed ligation assay for miRNA expression analysis that produces highly quantitative, 10-100 plex miRNA profiling in a single reaction. The inventive methods use a 2-step ligation assay to generate an array of miRNA specific ligation products that can be decoded and quantified by a size discrimination method such as gel electrophoresis or single molecule separation. One embodiment is a low-cost assay that can be performed using standard tools available in nearly all molecular biology laboratories. This assay requires nothing more than a gel apparatus and reader for detection. Other embodiments include use of magnetic beads and other size (Continued)

exclusion apparatus which give increasingly higher sensitivity, lower sample consumption, and reduced processing steps.

15 Claims, 8 Drawing Sheets

(51) Int. Cl.
| | | |
|---|---|---|
| C12M 1/34 | (2006.01) | |
| C07H 21/04 | (2006.01) | |
| C40B 30/04 | (2006.01) | |
| C40B 40/06 | (2006.01) | |
| G01N 31/22 | (2006.01) | |
| C12Q 1/25 | (2006.01) | |
| C12N 15/11 | (2006.01) | |

(52) U.S. Cl.
CPC ...... *C12Q 1/6813* (2013.01); *C12N 2310/141* (2013.01); *C12N 2320/10* (2013.01); *G01N 2333/9015* (2013.01)

(58) Field of Classification Search
USPC ....... 435/6.1, 6.12, 91.1, 91.2, 91.51, 91.52, 435/287.2; 536/24.3; 506/9, 16; 422/430
See application file for complete search history.

(56) References Cited

U.S. PATENT DOCUMENTS

| | | | | |
|---|---|---|---|---|
| 2008/0176233 | A1* | 7/2008 | Nilsen | C12Q 1/6816 435/6.12 |
| 2008/0194416 | A1* | 8/2008 | Chen | C12Q 1/6816 506/9 |
| 2009/0075276 | A1 | 3/2009 | Lee et al. | |
| 2010/0062436 | A1* | 3/2010 | Jarosch | C12Q 1/6816 435/6.14 |
| 2010/0062494 | A1* | 3/2010 | Church | C12N 15/1003 435/91.2 |
| 2011/0104693 | A1 | 5/2011 | Seligmann et al. | |
| 2012/0208707 | A1* | 8/2012 | Zeiner | C12N 9/93 506/2 |

FOREIGN PATENT DOCUMENTS

| | | |
|---|---|---|
| WO | 2008137466 A2 | 11/2008 |
| WO | 2009111643 A2 | 9/2009 |
| WO | 2009143379 A2 | 11/2009 |
| WO | 2011128900 A2 | 10/2011 |

OTHER PUBLICATIONS

Yan et al, Simple and sensitive detection of microRNAs with ligase chain reaction, 2010, Chem. Commun., 46, 2432-2434.*
Zhang, et al., "Sensitive detection of microrna with isothermal amplification and a single-quantum-dot-based nanosensor", Analytical Chemistry, vol. 86, No. 1, pp. 224-231, (Nov. 21, 2011).

* cited by examiner

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: synthetic sequence

<400> SEQUENCE: 1
actgtaggca ccatcaat                                         18

<210> SEQ ID NO 2
<211> LENGTH: 19
<212> TYPE: DNA
<213> ORGANISM: Artificial Sequence
<220> FEATURE:
<223> OTHER INFORMATION: synthetic sequence

<400> SEQUENCE: 2
actgtaggca ccatcaatc                                        19

<210> SEQ ID NO 3
<211> LENGTH: 19
<212> TYPE: DNA
<213> ORGANISM: Artificial Sequence
<220> FEATURE:
<223> OTHER INFORMATION: synthetic sequence

<400> SEQUENCE: 3
actgtaggca ccatcaatc                                        19

<210> SEQ ID NO 4
<211> LENGTH: 19
<212> TYPE: DNA
<213> ORGANISM: Artificial Sequence
<220> FEATURE:
<223> OTHER INFORMATION: synthetic sequence

<400> SEQUENCE: 4
gctgtaggca ccatcaatc                                        19

<210> SEQ ID NO 5
<211> LENGTH: 19
<212> TYPE: DNA
<213> ORGANISM: Artificial Sequence
<220> FEATURE:
<223> OTHER INFORMATION: synthetic sequence

<400> SEQUENCE: 5
uctgtaggca ccatcaatc                                        19

<210> SEQ ID NO 6
<211> LENGTH: 19
<212> TYPE: DNA
<213> ORGANISM: Artificial Sequence
<220> FEATURE:
<223> OTHER INFORMATION: synthetic sequence

<400> SEQUENCE: 6
cctgtaggca ccatcaatc                                        19

<210> SEQ ID NO 7
<211> LENGTH: 19
<212> TYPE: DNA
<213> ORGANISM: Artificial Sequence

```
<220> FEATURE:
<223> OTHER INFORMATION: synthetic sequence

<400> SEQUENCE: 7
actgtaggca ccatcaatc                                                        19

<210> SEQ ID NO 8
<211> LENGTH: 19
<212> TYPE: DNA
<213> ORGANISM: Artificial Sequence
<220> FEATURE:
<223> OTHER INFORMATION: synthetic sequence

<400> SEQUENCE: 8
actgtaggca ccatcaatc                                                        19

<210> SEQ ID NO 9
<211> LENGTH: 19
<212> TYPE: DNA
<213> ORGANISM: Artificial Sequence
<220> FEATURE:
<223> OTHER INFORMATION: synthetic sequence

<400> SEQUENCE: 9
gctgtaggca ccatcaatc                                                        19

<210> SEQ ID NO 10
<211> LENGTH: 19
<212> TYPE: DNA
<213> ORGANISM: Artificial Sequence
<220> FEATURE:
<223> OTHER INFORMATION: synthetic sequence

<400> SEQUENCE: 10
tctgtaggca ccatcaatc                                                        19

<210> SEQ ID NO 11
<211> LENGTH: 19
<212> TYPE: DNA
<213> ORGANISM: Artificial Sequence
<220> FEATURE:
<223> OTHER INFORMATION: synthetic sequence

<400> SEQUENCE: 11
cctgtaggca ccatcaatc                                                        19

<210> SEQ ID NO 12
<211> LENGTH: 19
<212> TYPE: DNA
<213> ORGANISM: Artificial Sequence
<220> FEATURE:
<223> OTHER INFORMATION: synthetic sequence

<400> SEQUENCE: 12
gattgatggt gcctacagt                                                        19

<210> SEQ ID NO 13
<211> LENGTH: 50
<212> TYPE: DNA
<213> ORGANISM: Artificial Sequence
<220> FEATURE:
<223> OTHER INFORMATION: synthetic sequence

<400> SEQUENCE: 13
acaaccagct aagacactgc caatcctgtt accatcgtag gcacctgaaa                      50
```

```
<210> SEQ ID NO 14
<211> LENGTH: 57
<212> TYPE: DNA
<213> ORGANISM: Artificial Sequence
<220> FEATURE:
<223> OTHER INFORMATION: synthetic sequence

<400> SEQUENCE: 14
aactatacaa cctactacct caatcctgtt accagtggct gctgccagtg gcgataa         57

<210> SEQ ID NO 15
<211> LENGTH: 64
<212> TYPE: DNA
<213> ORGANISM: Artificial Sequence
<220> FEATURE:
<223> OTHER INFORMATION: synthetic sequence

<400> SEQUENCE: 15
aacactgatt tcaaatggtg ctaatcctgt taccagtggc tgctgccatc gtaggcacct     60
gaaa                                                                  64

<210> SEQ ID NO 16
<211> LENGTH: 72
<212> TYPE: DNA
<213> ORGANISM: Artificial Sequence
<220> FEATURE:
<223> OTHER INFORMATION: synthetic sequence

<400> SEQUENCE: 16
cgccaatatt tacgtgctgc taatcctgtt accagtggct gctgccagtg gcgataagtc     60
gtgtcttacc gg                                                         72

<210> SEQ ID NO 17
<211> LENGTH: 82
<212> TYPE: DNA
<213> ORGANISM: Artificial Sequence
<220> FEATURE:
<223> OTHER INFORMATION: synthetic sequence

<400> SEQUENCE: 17
agcctatcct ggattacttg aaatcctgtt accagtggct gctgccagtg gcgataagtc     60
gtgtcatcgt aggcacctga aa                                              82

<210> SEQ ID NO 18
<211> LENGTH: 92
<212> TYPE: DNA
<213> ORGANISM: Artificial Sequence
<220> FEATURE:
<223> OTHER INFORMATION: synthetic sequence

<400> SEQUENCE: 18
tcaacatcag tctgataagc taatcctgtt accagtggct gctgccagtg gcgataagtc     60
gtgtcttacc gggttggact caagacgata gt                                   92
```

MIRNA ANALYSIS METHODS

REFERENCE TO RELATED APPLICATIONS

This application is a 35 U.S.C. §371 U.S. national entry of International Application PCT/US2013/025860 having an international filing date of Feb. 13, 2013, which claims the benefit of U.S. Provisional Application No. 61/598,513, filed Feb. 14, 2012, the content of each of the aforementioned applications is herein incorporated by reference in their entirety.

STATEMENT OF GOVERNMENTAL INTEREST

This invention was made with government support under grant numbers CA155305, GM103360, and CA151838 awarded by the National Institutes of Health. The government has certain rights in the invention.

INCORPORATION-BY-REFERENCE OF MATERIAL SUBMITTED ELECTRONICALLY

The instant application contains a Sequence Listing which has been submitted in ASCII format via EFS-Web and is hereby incorporated by reference in its entirety. Said ASCII copy, created on Aug. 13, 2014, is named P11885-03_ST25.txt and is 4,013 bytes in size.

BACKGROUND OF THE INVENTION

MicroRNAs (miRNA) are short, noncoding RNAs with pervasive roles throughout gene expression in cellular processes such as differentiation and disease states such as cancer. Uncovering the roles of these molecules in development and tumorigenesis are key steps to the discovery of robust, new biomarkers and potential disease cures.

Existing methods to analyze miRNA expression consist of single-target PCR based methods and highly multiplexed array methods. PCR is very sensitive but can only analyze a single target. Thus, detection of miRNA panels requires large numbers of parallel reactions, greatly increasing cost, sample consumption, and complexity. Existing array based methods can analyze hundreds of miRNA in a single reaction but have high cost per sample, low sample throughput, and limited sensitivity. Successful clinical validation and translation of these promising miRNA panels will require that 10-100 miRNA be accurately quantified in a cost-effective, high-throughput, and robust manner. No existing technology can bridge this gap between the highly multiplexed but expensive array-based methods and the sensitive but singleplex qPCR methods. Currently, no method is able to achieve the high sensitivity, multiplex detection necessary for low cost miRNA profiling in rare clinical samples.

Thus, there exists a need for a low cost, PCR-free, multiplexed assay for miRNA expression analysis that performs highly quantitative, 10-100 plex miRNA profiling in a single reaction in less time than currently existing methods.

SUMMARY OF THE INVENTION

To address this need, the inventors have developed an inexpensive and facile multiplex, ligation assay targeting short RNA sequences, such as miRNA for RNA profiling.

In accordance with one or more embodiments the present invention provides novel compositions and methods for miRNA analysis. These inventive compositions and methods are collectively named the "Ligo-miR™" assays.

In an embodiment termed the "Ligo-miR EZ assay", the embodiment leverages the high multiplex capability and high specificity of the ligation mechanism for PCR-free and RT-free analysis of miRNAs in rare clinical samples. The methods of the present invention use a 2-step ligation process to create a fast (~4 hours), sensitive (<$10^{-18}$ moles), and highly specific (>1000:1) miRNA profiling tool. When compared to the dominant microarray technologies, assay cost will be 20-fold less, assay times will be 5-fold shorter, and sensitivity will be 100-fold higher.

The compositions and methods of the present invention use a novel 2-step ligation process to generate size encoded miRNA ligation products that can be individually identified and quantified by gel separation (Ligo-miR EZ), single molecule analysis (termed "Ligo-miR HD"), capillary electrophoresis, chromatography, or any other nucleic acid sizing method. A 50 cycle linear amplification (non-PCR) can be integrated into the second ligation step to boost sensitivity while maintaining excellent linearity.

In one or more embodiments, the present invention provides methods for detecting miRNA biomarkers in the blood, serum, sputum, urine, stool, or other body fluid of subjects, which comprise a noninvasive diagnostic or prognostic technology that is sufficiently sensitive to detect or predict the outcome or response of disease states such as oncogenic, cancerous, premalignant or metaplastic changes in a biological sample of a mammalian subject.

In one or more embodiments, the present invention provides methods for detecting miRNA biomarkers in the tissue of subjects, which comprise a diagnostic or prognostic technology that is sufficiently sensitive to detect or predict the outcome or response of disease states such as oncogenic, cancerous, premalignant or metaplastic changes in a biological sample of a mammalian subject.

In accordance with an embodiment, the present invention provides a method for detection of one or more target RNA of interest in a sample comprising: a) obtaining a sample containing one or more target RNA of interest; b) adding to the sample of a) a sufficient amount of adapter probes and a sufficient amount of a first ligase c) performing a first ligation step by incubation and allowing the adapter probes to be ligated to the 3'-OH ends of the one or more target RNA of interest in the sample; d) adding to the sample of b) a sufficient amount of common probes and discrimination probes, and a sufficient amount of a second ligase; e) performing a second ligation step by incubating the sample of c) for a sufficient amount of time to effect hybridization of probes of d) with ligated target RNA of interest and adapter probes of b) and to allow ligation between the discrimination probes and common probes; and f) analysis of the products of by one or more size discrimination methods.

In accordance with another embodiment, the present invention provides a method for detection of one or more a target RNA of interest in a sample comprising: a) obtaining a sample containing one or more target RNA of interest; b) adding to the sample of a) a sufficient amount of adapter probes and a sufficient amount of a first ligase and allowing the adapter probes to be ligated to the 3'-OH ends of the one or more target RNA of interest in the sample; c) adding to the sample of b) a sufficient amount of common probes and discrimination probes, and a sufficient amount of a second ligase; d) thermocycling the sample of c) for a sufficient amount of time to effect hybridization of probes of c) with ligated target RNAs of interest and adapter probes of b) and to allow ligation between the discrimination probes and common probes; e) separation of the products of d) by gel electrophoresis; f) detecting the products of e) through imaging of the gel.

In accordance with a further embodiment, the present invention provides a method for detection of one or more miRNA of interest in a sample comprising: a) obtaining a sample containing one or more miRNA of interest; b) adding to the sample of a) a sufficient amount of adapter probes and a sufficient amount of a first ligase and allowing the adapter probes to be ligated to the 3'-OH ends of the one or more miRNA of interest in the sample; c) adding to the sample of b) a sufficient amount of common probes and discrimination probes, and a sufficient amount of a second ligase; d) thermocycling the sample of c) for a sufficient amount of time to effect hybridization of probes of c) with ligated miRNA of interest and adapter probes of b) and to allow ligation between the discrimination probes and common probes; e) analysis of the products by size discrimination.

In accordance with an embodiment, the present invention provides a method for detection of one or more miRNA of interest in a sample comprising: a) obtaining a sample containing one or more miRNA of interest; b) adding to the sample of a) a sufficient amount of adapter probes and a sufficient amount of a first ligase and allowing the adapter probes to be ligated to the 3'-OH ends of the one or more miRNA of interest in the sample; c) adding to the sample of b) a sufficient amount of common probes and discrimination probes, and a sufficient amount of a second ligase; d) thermocycling the sample of c) for a sufficient amount of time to effect hybridization of probes of c) with ligated miRNAs of interest and adapter probes of b) and to allow ligation between the discrimination probes and common probes; e) separation of the products of d) using single molecule free solution hydrodynamic separation (SML-FSHS); f) detecting the products of e) through analysis of peaks in the resulting chromatograph.

In accordance with a further embodiment, the present invention provides a method for detection of one or more miRNA of interest in a sample comprising: a) obtaining a sample containing one or more miRNA of interest; b) adding to the sample of a) a sufficient amount of adapter probes bound to a plurality of magnetic particles, and a sufficient amount of a first ligase and allowing the adapter probes bound to the magnetic particles to be ligated to the 3'-OH ends of the one or more miRNA of interest in the sample; c) magnetically isolating the particles having the miRNA of interest ligated to the bound adapter probes; d) washing the particles of c) and resuspending the particles in buffer; e) adding to a sample of the particles of d)) a sufficient amount of common probes and discrimination probes, and a sufficient amount of a second ligase, and water; f) thermocycling the sample of e) for a sufficient amount of time to effect hybridization of probes of e) with ligated miRNAs of interest and adapter probes of b) and to allow ligation between the discrimination probes and common probes; g) separation of the products off) by gel electrophoresis; h) detecting the products of g) through imaging of the gel.

In accordance with another embodiment, the present invention provides a method for high efficiency and low bias ligation of an adapter probe to a short RNA sequence comprising: a) obtaining a sample containing one or more target RNA of interest; b) adding to the sample a saturating amount of adapter probe; c) adding to the sample a saturating amount of ligase; d) adding to the sample a saturating amount of PEG; and e) performing a ligation step by incubation and allowing the adapter probes to be ligated to the 3'-OH ends of the one or more target RNA of interest in the sample.

In accordance with an embodiment, the present invention provides methods of diagnosis of the presence of a disease in a subject comprising obtaining a biological sample from the subject and measuring the expression levels of one or more miRNAs of interest which are associated with the presence of the disease or condition using the methods of the present invention.

In accordance with an embodiment, the present invention provides methods of generating a miRNA profile of at least one or more tumors in a subject comprising obtaining a biological sample from the subject and measuring the expression levels of one or more miRNAs of interest which are associated with a particular cancer profile using the methods of the present invention.

DETAILED DESCRIPTION OF THE INVENTION

Figure 1:
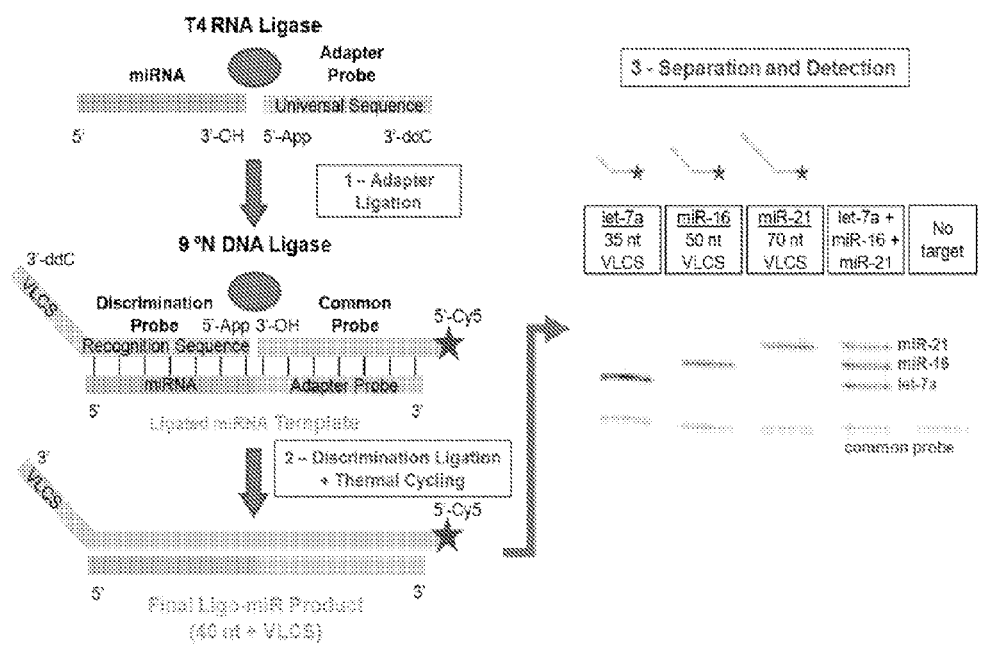
FIG. 1 shows a schematic of the overall Ligo-miR™ analysis methods of the present invention.

By "nucleic acid" as used herein includes "polynucleotide," "oligonucleotide," and "nucleic acid molecule," and generally means a polymer of DNA or RNA, which can be single-stranded or double-stranded, synthesized or obtained (e.g., isolated and/or purified) from natural sources, which can contain natural, non-natural or altered nucleotides, and which can contain a natural, non-natural or altered internucleotide linkage, such as a phosphoroamidate linkage or a phosphorothioate linkage, instead of the phosphodiester found between the nucleotides of an unmodified oligonucleotide. It is generally preferred that the nucleic acid does not comprise any insertions, deletions, inversions, and/or substitutions. However, it may be suitable in some instances, as discussed herein, for the nucleic acid to comprise one or more insertions, deletions, inversions, and/or substitutions.

In an embodiment, the nucleic acids of the invention are recombinant. As used herein, the term "recombinant" refers to (i) molecules that are constructed outside living cells by joining natural or synthetic nucleic acid segments to nucleic acid molecules that can replicate in a living cell, or (ii) molecules that result from the replication of those described in (i) above. For purposes herein, the replication can be in vitro replication or in vivo replication.

As used herein, the term "target RNA of interest" can be any short ribonucleic acid sequence. The length of such a target RNA sequence is from about 8 to about 100 nucleotides. In some embodiments, the target RNA could be longer that 100 nucleotides. Examples of target RNAs include miRNA, siRNA and other RNA sequences that are useful in diagnosis and treatment of disease and other uses. In accordance with an embodiment, the target RNA of interest is miRNA.

The nucleic acids used as primers in embodiments of the present invention can be constructed based on chemical synthesis and/or enzymatic ligation reactions using procedures known in the art. See, for example, Sambrook et al. (eds.), *Molecular Cloning, A Laboratory Manual*, 3$^{rd}$ Edition, Cold Spring Harbor Laboratory Press, New York (2001) and Ausubel et al., *Current Protocols in Molecular Biology*, Greene Publishing Associates and John Wiley & Sons, NY (1994). For example, a nucleic acid can be chemically synthesized using naturally occurring nucleotides or variously modified nucleotides designed to increase the biological stability of the molecules or to increase the physical stability of the duplex formed upon hybridization (e.g., phosphorothioate derivatives and acridine substituted nucleotides). Examples of modified nucleotides that can be used to generate the nucleic acids include, but are not limited to, 5-fluorouracil, 5-bromouracil, 5-chlorouracil, 5-iodouracil, hypoxanthine, xanthine, 4-acetylcytosine, 5-(carboxyhydroxymethyl) uracil, 5-carboxymethylaminomethyl-2-thiouridine, 5-carboxymethylaminomethyluracil, dihydrouracil, beta-D-galactosylqueosine, inosine, $N^6$-isopentenyladenine, 1-methylguanine, 1-methylinosine, 2,2-dimethylguanine, 2-methyladenine, 2-methylguanine, 3-methylcytosine, 5-methylcytosine, $N^6$-substituted adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, 3-(3-amino-3-N-2-carboxypropyl) uracil, and 2,6-diaminopurine. Alternatively, one or more of the nucleic acids of the invention can be purchased from companies, such as Integrated DNA Technologies (Coralville, Iowa) and Genscript (Piscataway, N.J.).

The term "isolated and purified" as used herein means a protein that is essentially free of association with other proteins or polypeptides, e.g., as a naturally occurring protein that has been separated from cellular and other contaminants by the use of antibodies or other methods or as a purification product of a recombinant host cell culture.

The term "biologically active" as used herein means an enzyme or protein having structural, regulatory, or biochemical functions of a naturally occurring molecule.

As used herein, the term "subject" refers to any mammal, including, but not limited to, mammals of the order Rodentia, such as mice and hamsters, and mammals of the order Logomorpha, such as rabbits. It is preferred that the mammals are from the order Carnivora, including Felines (cats) and Canines (dogs). It is more preferred that the mammals are from the order Artiodactyla, including Bovines (cows) and Swines (pigs) or of the order Perssodactyla, including Equines (horses). It is most preferred that the mammals are of the order Primates, Ceboids, or Simoids (monkeys) or of the order Anthropoids (humans and apes). An especially preferred mammal is the human.

In accordance with an embodiment, the present invention provides A method for detection of one or more target RNA of interest in a sample comprising: a) obtaining a sample containing one or more target RNA of interest; b) adding to the sample of a) a sufficient amount of adapter probes and a sufficient amount of a first ligase c) performing a first ligation step by incubation and allowing the adapter probes to be ligated to the 3'-OH ends of the one or more target RNA of interest in the sample; d) adding to the sample of b) a sufficient amount of common probes and discrimination probes, and a sufficient amount of a second ligase; e) performing a second ligation step by incubating the sample of c) for a sufficient amount of time to effect hybridization of probes of c) with ligated target RNA of interest and adapter probes of b) and to allow ligation between the discrimination probes and common probes; f) analyzing the products of d) by a size discrimination method.

Size discrimination methods used in accordance with the inventive methods can be any techniques known in the art, such as, for example, gel electrophoresis, capillary electrophoresis, high pressure liquid chromatography, mass spectrometry, fluorescence spectroscopy, and other methods.

It will be understood by those of ordinary skill in the art that the inventive methods disclosed herein are capable of both detecting the target RNA of interest as well as quantifying the amount of target RNA in a sample. The quantification of target RNA of interest allows elucidation of expression levels of the target RNA in the sample.

In some embodiments of the above method, the adapter probe is bound to a magnetic bead at the 3' end.

In some alternate embodiments of the above method, a magnetic separation, wash, and resuspension are performed after c) first ligation step. It will be understood by those of ordinary skill, that the magnetic beads and methods using them in separations are those commonly used in the art.

In accordance with one or more embodiments, the inventive methods can include heat denaturing steps are performed post c) the first ligation step and e) the second ligation step. Heat denaturing, as used herein, can include direct heat and incubation of the sample for a set period of time, or can be accomplished through the use of a thermocycling apparatus commonly used in the nucleic acid arts. In some embodiments, the incubation step comprises thermocycling between 1-100 cycles of between about 0.25 to about 5 minutes @ 45° C. to about 95° C. denaturation followed by between about 0.25 to about 100 minutes @ 4° C. to about 80° C. ligation. In a preferred embodiment, the incubation step comprises thermocycling between 1-100 cycles of about 30 s @ 95° C. denaturation followed by about 30 s @ 45° C. ligation.

In accordance with one or more embodiments, the inventive methods can also include PCR amplification of the reaction products is performed after e) the second ligation step but before f) size discrimination.

In alternative embodiments which include PCR amplification, one PCR primer is anti-sense to the VLCS sequence and the second primer is anti-sense to the adapter probe sequence.

In accordance with one or more embodiments, the inventive methods can be used to identify target RNA of interest, including miRNA, siRNA, or other RNA sequences comprising between 8 to 150 nucleotides in length.

It will be understood by those of ordinary skill in the art that the methods of the present invention comprise two general steps. The first step being the first ligation step wherein the target RNA of interest is incubated with the adapter probes and allowing the adapter probes to be ligated to the 3'-OH ends of the one or more target RNA of interest in the sample. The second general step being the second ligation step wherein the addition to the sample, a sufficient amount of common probes and discrimination probes, and a sufficient amount of a second ligase, and incubating the sample for a sufficient amount of time to effect hybridization of probes with ligated target RNA of interest and adapter probes and to allow ligation between the discrimination probes and common probes. In accordance with some embodiments, the two steps of these methods can be separated and performed at substantially different times. For example, the first step can be applied to a sample and stored for later analysis using the second step.

In alternative embodiments, only the first step is applied to the sample and then alternative analytical methods can be applied, such as PCR, qPCR, microarray, sequencing, or other methods known in the art. Due to their short length, the first step of nearly all microRNA analysis techniques is to lengthen the microRNA target through either poly(A)-tailing or, more commonly, ligation. MicroRNA capture through adapter probe ligation is the pervasive first step in the majority of PCR-, microarray-, multiplexing-, and sequencing-based assays. However, this ligation can introduce substantial bias to the resultant to microRNA expression profile analysis. This inventive embodiment enables the downstream assessment of high fidelity expression profiles, using any number of techniques, that are largely free from the blurring effects of ligation bias due to the high efficiency and low bias adapter ligation. Key assay parameters such as PEG %, adapter probe concentration, ligase type, ligase amount, incubation time, incubation temperature, and adapter probe design are used to reduce ligation preference.

In an alternative embodiment, 100-1000 units of ligase, 1-12 pmol adenylated adapter probe, 10-40% PEG8000 or PEG4000, and T4 RNA ligase reaction buffer (New England Biolabs) are added to 1-10,000 ng of total RNA to form a 5-100 μL reaction mixture. The reaction is incubated at 4-95° C. for 0.25-24 hours. Potential ligases comprise T4 RNA ligase 1, T4 RNA ligase 2 truncated, T4 RNA ligase 2 K227Q, T4 RNA ligase 2 truncated KQ, and Mth. RNA ligase.

In an alternative embodiment, 200-400 units of T4 RNA Ligase 2 truncated K227Q, 4-8 pmol adenylated adapter probe, 20-30% PEG8000 or PEG4000, and T4 RNA ligase reaction buffer (New England Biolabs) are added to 100-1000 ng of total RNA to form a 10-30 μL reaction mixture. The reaction is incubated at 4-37° C. for 1-8 hours.

In yet another alternative embodiment, 300 units of T4 RNA Ligase 2 truncated K227Q, 6 pmol adenylated adapter probe, 25% PEG8000, and T4 RNA ligase reaction buffer (New England Biolabs) are added to 500 ng of total RNA to form a 20 μL reaction mixture. The reaction is incubated at 25° C. for 4 hours.

Figure 8:
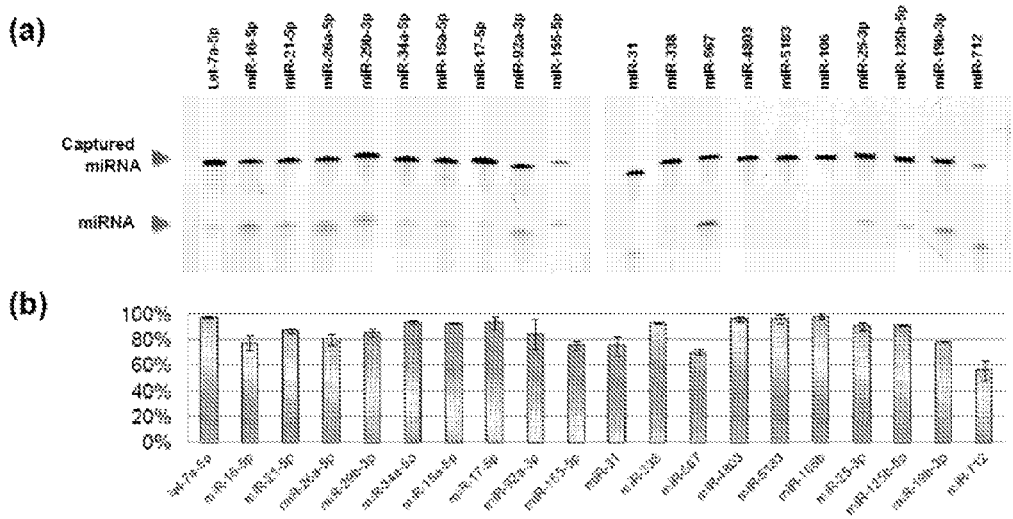
FIG. 8 shows a gel image and capture efficiency analysis from adapter probe ligation to miRNA using the high efficiency and low bias first step ligation only. (a) Cy3-labeled miRNAs were captured using an optimized protocol. All miRNAs are uniformly captured with high efficiency. (c) Quantified miRNA capture efficiency of (a).

In an alternative embodiment, the adapter probe is comprised of DNA bases. In another embodiment, the adapter probe is comprised of a mixture of DNA and RNA bases. In yet another embodiment, the adapter probe is comprised of RNA bases at or near the ligation site. As shown in FIG. 8, this method is able to achieve high efficiency (85% average capture efficiency) and low bias (11% CV) across a 20-plex miRNA panel. Such high efficiency and low bias has not previously been achieved. By using a PEG8000 level that is substantially higher than commonly recommended (25% vs. 15%), saturating adapter probe levels (>6 pmol for 500 ng of total RNA), and a saturating enzyme amount (>300 units for 500 ng of total RNA), ligation efficiency is greatly enhanced and bias is significantly suppressed. Examples of adapter probe sequences are given in Table 1.

In alternative embodiments, only the second step is applied to the sample and alternative analytical methods are applied to the microRNA beforehand such as reverse transcription or poly (A) tailing.

In accordance with one or more embodiments of the present invention, it will be understood that the types of cancer diagnosis which may be made, using the methods provided herein, is not necessarily limited. For purposes herein, the cancer can be any cancer. As used herein, the term "cancer" is meant any malignant growth or tumor caused by abnormal and uncontrolled cell division that may spread to other parts of the body through the lymphatic system or the blood stream.

The cancer can be a metastatic cancer or a non-metastatic (e.g., localized) cancer. As used herein, the term "metastatic cancer" refers to a cancer in which cells of the cancer have metastasized, e.g., the cancer is characterized by metastasis of a cancer cells. The metastasis can be regional metastasis or distant metastasis, as described herein.

Other diseases or conditions where analysis of miRNA and other RNA using the methods of the present invention can be applied include cardiovascular disease, liver disease, neurological disorders, psychiatric disorders, diabetes, sepsis, arthritis, viral infection, Alzheimer disease, and immune disorders.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the inventive methods can provide any amount of any level of diagnosis, staging, screening, or other patient management, including treatment or prevention of cancer in a mammal. Furthermore, the treatment or prevention provided by the inventive method can include treatment or prevention of one or more conditions or symptoms of the disease, e.g., cancer, being treated or prevented. Also, for purposes herein, "prevention" can encompass delaying the onset of the disease, or a symptom or condition thereof.

"Complement" or "complementary" as used herein to refer to a nucleic acid may mean Watson-Crick (e.g., A-T/U and C-G) or Hoogsteen base pairing between nucleotides or nucleotide analogs of nucleic acid molecules.

"Identical" or "identity" as used herein in the context of two or more nucleic acids or polypeptide sequences may mean that the sequences have a specified percentage of residues that are the same over a specified region. The percentage may be calculated by optimally aligning the two sequences, comparing the two sequences over the specified region, determining the number of positions at which the identical residue occurs in both sequences to yield the number of matched positions, dividing the number of matched positions by the total number of positions in the specified region, and multiplying the result by 100 to yield the percentage of sequence identity. In cases where the two sequences are of different lengths or the alignment produces one or more staggered ends and the specified region of comparison includes only a single sequence, the residues of single sequence are included in the denominator but not the numerator of the calculation. When comparing DNA and RNA, thymine (T) and uracil (U) may be considered equivalent. Identity may be performed manually or by using a computer sequence algorithm such as BLAST or BLAST 2.0.

"Probe" as used herein may mean an oligonucleotide capable of binding to a target nucleic acid of complementary sequence through one or more types of chemical bonds, usually through complementary base pairing, usually through hydrogen bond formation. Probes may bind target sequences lacking complete complementarity with the probe sequence depending upon the stringency of the hybridization conditions. There may be any number of base pair mismatches which will interfere with hybridization between the target sequence and the single stranded nucleic acids described herein. However, if the number of mutations is so great that no hybridization can occur under even the least stringent of hybridization conditions, the sequence is not a complementary target sequence. A probe may be single stranded or partially single and partially double stranded. The strandedness of the probe is dictated by the structure, composition, and properties of the target sequence. Probes may be directly labeled or indirectly labeled such as with biotin to which a streptavidin complex may later bind.

"Substantially complementary" used herein may mean that a first sequence is at least 60%, 65%, 70%, 75%, 80%, 85%, 90%, 95%, 97%, 98% or 99% identical to the complement of a second sequence over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides, or that the two sequences hybridize under stringent hybridization conditions.

"Substantially identical" used herein may mean that a first and second sequence are at least 60%, 65%, 70%, 75%, 80%, 85%, 90%, 95%, 97%, 98% or 99% identical over a region of 8, 9, 10, 11, 12, 13, 14, 15, 16, 17, 18, 19, 20, 21, 22, 23, 24, 25, 30, 35, 40, 45, 50, 55, 60, 65, 70, 75, 80, 85, 90, 95, 100 or more nucleotides or amino acids, or with respect to nucleic acids, if the first sequence is substantially complementary to the complement of the second sequence.

"Target" as used herein can mean an oligonucleotide or portions or fragments thereof, which may be bound by one or more probes under stringent hybridization conditions. "Target" as used herein may also mean a specific miRNA or portions or fragments thereof, which may be bound by one or more probes under stringent hybridization conditions.

The nucleic acids of the present invention may also comprise a sequence of a miRNA or a variant thereof. The miRNA sequence may comprise from 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 50, 60, 70, 80, 90 and up to 100 nucleotides. The sequence of the miRNA may be the first 13-33 nucleotides of the pre-miRNA. The sequence of the miRNA may also be the last 13-33 nucleotides of the pre-miRNA.

As used herein, the term "a first ligase and/or second ligase" means many different types of ligase can be used in accordance with the methods of the present invention. Examples of such ligases include E. Coli DNA ligase, Taq DNA ligase, 9° N DNA ligase, T4 DNA ligase, T4 RNA ligase 1, T4 RNA ligase 2, Ampligase, genetically modified variants of natural DNA/RNA ligases, and others known in the art.

In accordance with one or more embodiments, the concentrations of reagents such as ligases and probes can be in "saturating amounts." As used herein, a saturating amount of reagent (enzyme, probe, reaction time, etc.) is the point at which increasing beyond that point causes no further increase in reaction efficiency. That point is found by spiking each miRNA into a background of total RNA and slowly increasing the parameter (enzyme, probe, reaction time) until no further increase in miRNA capture efficiency is seen. It is critical that this is performed while spiking into a total RNA background as opposed to pure buffer because the optimum conditions obtained using a total RNA background are quite different than those obtained using a buffer background.

In accordance with one or more embodiments, additives can be used in the methods of the present invention. For example, additives such as PEG or DMSO are added to increase ligation efficiency and reduce ligation bias.

In accordance with one or more embodiments, internal controls are added to account for variations in ligation efficiency.

A method of identifying a nucleic acid associated with a disease or a pathological condition is also provided. The method comprises measuring a level of the nucleic acid in a sample that is different than the level of a control. In accordance with an embodiment, the nucleic acid is a miRNA and the detection may be performed by contacting the sample with a probe or biochip described herein and detecting the amount of hybridized product.

The level of the nucleic acid in the sample may also be compared to a control cell (e.g., a normal cell) to determine whether the nucleic acid is differentially expressed (e.g., overexpressed or underexpressed). The ability to identify miRNAs that are differentially expressed in pathological cells compared to a control can provide high-resolution, high-sensitivity datasets which may be used in the areas of diagnostics, prognostics, therapeutics, drug development, pharmacogenetics, biosensor development, and other related areas.

The expression level of a disease-associated nucleic acid or miRNA provides information in a number of ways. For example, a differential expression of a disease-associated nucleic acid compared to a control may be used as a diagnostic that a patient suffers from the disease. Expression levels of a disease-associated nucleic acid may also be used to monitor the treatment and disease state of a patient. Furthermore, expression levels of a disease-associated miRNA may allow the screening of drug candidates for altering a particular expression profile or suppressing an expression profile associated with disease.

A target nucleic acid or portions or fragments thereof, may be detected and levels of the target nucleic acid measured by contacting a sample comprising the target nucleic acid with a biochip comprising an attached probe sufficiently complementary to the target nucleic acid and detecting hybridization to the probe above control levels.

In accordance with another embodiment of the present invention, it will be understood that the term "biological sample" or "biological fluid" includes, but is not limited to, any quantity of a substance from a living or formerly living patient or mammal Such substances include, but are not limited to, blood, serum, plasma, urine, cells, organs, tissues, bone, bone marrow, lymph, lymph nodes, synovial tissue, chondrocytes, synovial macrophages, endothelial cells, and skin. In a preferred embodiment, the fluid is blood or serum.

A method of diagnosis is also provided. The method comprises detecting a differential expression level of two or more disease-associated miRNAs in a biological sample. The sample may be derived from a subject. Diagnosis of a disease state in a subject may allow for prognosis and selection of therapeutic strategy. Further, the developmental stage of cells may be classified by determining temporarily expressed disease-associated miRNAs.

In accordance with an embodiment, the present invention provides methods for diagnosis of a disease or condition in a subject comprising: a) obtaining a biological sample from the subject; b) analyzing the sample of a) for one or more target RNA of interest using the methods described above; c) comparing the expression levels of the one or more target RNA of interest in the sample to the expression levels of the one or more target RNA of interest in a control sample; d) diagnosing the subject as having the disease or condition when detecting the expression levels of one or more target RNA of interest which are associated with the presence of the disease or condition in the sample of the subject when compared to the control sample.

In some embodiments of the methods for diagnosis of a disease or condition in a subject, the target RNA is miRNA, siRNA or other RNA sequences comprising between 8 to 150 nucleotides in length.

The identity and relative quantity of miRNAs in a sample can be used to provide a miRNA profiles for a particular sample. A miRNA profile for a sample includes information about the identities of miRNAs contained in the sample, quantitative levels of miRNAs contained in the sample, and/or changes in quantitative levels of miRNAs relative to another sample. For example, a miRNA profile for a sample includes information about the identities, quantitative levels, and/or changes in quantitative levels of miRNAs associated a particular cellular type, process, condition of interest, or other cellular state. Such information can be used, for diagnostic purposes, drug development, drug screening and/or drug efficacy testing.

In another example, with regard to diagnostics, if it is known that the presence or absence of a particular miRNA or group of miRNAs is associated with the presence or absence of a particular condition of interest, then a diagnosis of the condition can be made by obtaining the miRNA profile of a sample taken from a patient being diagnosed.

EXAMPLES

Fundamental Ligo-miR™ Assay Principles. In accordance with one or more embodiments, the inventive Ligo-miR™ methods provided herein comprise a PCR-free, 2-step ligation assay for multiplex miRNA detection that encodes and detects miRNA of interest based on probe length. In a first ligation step, a universal adapter probe is ligated to the 3'-OH of every miRNA in a sample using a first ligase to form a ligated oligonucleotide template. In a second ligation step, miRNA of interest specific discrimination probes and a universal common probe are then added to the solution and allowed to hybridize to the miRNA-adapter templates and ligated using a second ligase to form the final Ligo-miR™ reaction products.

In accordance with an embodiment, the common probe and adapter probe are complementary to each other and shared across all miRNA. Each discrimination probe is specifically complimentary to each miRNA of interest at the 5' end, and which also comprises a variable length coding sequence portion (VLCS) at its 3' end. Each discrimination probe comprises a corresponding 5-150 nt VLCS that is used to identify the specific miRNA probe by its unique length using size discrimination methods such as electrophoresis. Thus, in a set of probes to be used for multiplex miRNA detection there will be 1 discrimination probe for each miRNA of interest being detected, a single adapter probe and a single common probe. Only in the presence of the specific miRNA of interest, will the specific discrimination probe and common probe be ligated together in the second step. This 2-step ligation process ensures that only mature miRNA are detected with high specificity. In the first ligation step, the adapter probe must be ligated immediately adjacent to the mature miRNA sequence for the second ligation step to even occur.

Detection of Ligo-miR™ Reaction Products. In accordance with another embodiment, the analysis of the reaction products is performed through detection of the fluorescent label attached to the 5' end of the common probe. Each specific miRNA leads to a corresponding reaction product which is then identified by length. In accordance with an alternative embodiment, the discrimination probes are additionally fluorescently labeled at the 3' end. Analysis of the products is performed through coincidence analysis of the 3' discrimination probe signal and the 5' common probe signal that occurs only when ligation has occurred.

In accordance with a further embodiment, the discrimination probes and common probe are labeled with fluorescent dyes such that fluorescent resonance energy transfer (FRET) occurs when the ligation product has formed.

In accordance with still another embodiment, the discrimination probes are internally labeled rather than end labeled. The discrimination probes can be labeled with the same or different labels as well.

It will be understood by those of skill in the art that in certain embodiments, the probes are detectably labeled by any known means, including, for example, radio-labeled, fluorescently labeled, colorimetrically labeled, etc.

In accordance with the inventive methods, the detection of the hybridized product length can be performed by gel electrophoresis, capillary electrophoresis, free solution hydrodynamic separation, chromatography methods, etc.

Alternative variations of Ligo-miR™ assay methods of the present invention. In accordance with an embodiment, a single adapter probe, a single common probe, and a set of discrimination probes are designed to perform multiplex detection where the position of the second ligation site, on the opposite strand, is exactly opposite the first ligation site. In accordance with another embodiment, the second ligation site is shifted in either the 3' or 5' direction such that it is offset from the first ligation site to increase specificity.

In accordance with yet another embodiment, the second ligation site is shifted and multiple common probes, multiple adapter probes, and a set of discrimination probes are designed to enable multiplexing by color and length.

In accordance with one or more embodiments, the first ligation is performed in the absence of ATP.

In accordance with one or more embodiments, the second ligation is performed in the absence of ATP.

In accordance with a further embodiment, polymerase chain reaction (PCR) primer sites are designed into the probe sequences to enable incorporation of a downstream PCR amplification step. The 3' end of all the discrimination probes are designed to contain a common PCR primer site. A forward primer, anti-sense to this site, is synthesized. A reverse primer, anti-sense to the adapter probe sequence, is also synthesized. In this manner, all the miRNA specific ligation products can be PCR amplified using a single PCR primer set. PCR amplification is performed after the second ligation step by adding the aforementioned PCR primers, polymerase, and PCR reagents to the ligation products and thermocycling. The discrimination probes for miR-26a, miR-34a, and miR-29b listed in Table 1 include such a common PCR primer site.

In accordance with still another embodiment, poly(A) tailing is used in the first step instead of ligation and a poly(T) common probe is used is the second step. A sufficient amount of poly(A) polymerase, poly(A) polymerase reaction buffer, and ATP are added to the sample containing the RNA of interest and incubated at 37° C. for 10 minutes. This adds a poly(A) tail to the end of each RNA molecule in the sample. The polymerase is then heat inactivated at 65° C. for 20 minutes. A poly(T) common probe is then used and the assay proceeds accordingly. In yet another embodiment 5 units of poly(A) polymerase, 1× poly(A) polymerase reaction buffer, and 1 mM ATP are added to 500 ng of total RNA and incubated at 37° C. for 10 minutes.

Adapter Probe Design. The adapter probes used in the methods of the present invention are commercially synthesized, HPLC or PAGE purified, DNA oligonucleotides. In accordance with an embodiment, a typical adapter probe is about 19 nt in length with a 5'-App (adenylation) and 3'-ddC (dideoxycytosine).

In accordance with another embodiment, the 3' terminus of the adapter probe is blocked by -ddC to prevent unwanted ligation products. Other blocking moieties known in the art may also be used, for example, an $NH_2$ moiety.

In accordance with one or more alternative embodiments, the 3' terminus may also be labeled with a detectable moiety known in the art, for example, an indicator such as Cy3, Cy5, Alexa488, Alexa647, FITC, etc. can be used.

In accordance with one or more embodiments, the adapter probe comprises a detectable internal label.

In accordance with one or more embodiments, the 5' terminus of the adapter probe is pre-adenylated so that ligation can be performed in the absence of ATP, reducing unwanted ligation products. Pre-adenylation can be performed using known methods either enzymatically or chemically.

In accordance with another embodiment, the 5' residue is RNA rather than DNA to reduce ligation bias and to increase ligation efficiency.

In accordance with still another embodiment, alternative nucleic acid residues such as locked nucleic acids (LNAs) or peptide nucleic acids (PNAs) may be substituted at various positions to increase binding specificity. It will be understood by those of ordinary skill in the art that LNAs can significantly enhance the binding characteristics of nucleic acid probes. LNA bases can be substituted into the recognition sequence of the discrimination probes as well as the adapter and/or common probes. The substitution of LNA bases raises the overall melting temperatures of the individual probes. Such a strategy can be used to: 1) increase probe specificity for distinguishing closely related miRNA, 2) matching probe melting temperatures to minimize variability in reaction efficiency, and 3) increasing overall reaction efficiency by increasing probe binding strength. Peptide nucleic acids can be used similarly.

The adapter probe sequences of the present invention can be designed to either eliminate or promote formation of secondary structures, either alone, or in conjunction with the miRNA targets of interest. Such secondary structures can be useful in reducing or increasing ligation efficiency as appropriate. Typical adapter probe sequences are provided in Table 1.

In accordance with one or more embodiments, the adapter probe comprises a biotin or streptavidin at the 3' end.

In accordance with one or more embodiments, the adapter probe is bound to a magnetic bead at the 3' end.

In accordance with one or more embodiments, wherein the adapter probe is comprised of RNA nucleotides.

Common Probe Design. In accordance with one or more embodiments of the present invention, the common probes are commercially synthesized, HPLC or PAGE purified, DNA oligonucleotides. In accordance with an embodiment, typically, a single common probe is utilized in each probe set. A typical common probe is about 19 nt in length with a sequence that is complimentary to the adapter probe, and has a detectable moiety on the 5' end, for example, 5'-Cy5, and also comprises a 3'-OH end. In an alternative embodiment, the 5' end of the common probe of the present invention can be labeled with other detectable moieties, such as Cy3, Alexa488, Alexa 647, FITC, fluorescein, etc.

In accordance with one or more embodiments, the common probe comprises 10-30 DNA nucleotides in length and is complementary to the adapter probe sequence and further comprises a 3'-OH.

In accordance with one or more embodiments, the common probe comprises a detectable internal label.

In accordance with another embodiment, alternative nucleic acid residues such as locked nucleic acids or peptide nucleic acids may be substituted at various positions to increase binding specificity.

It will be understood by those of ordinary skill in the art that the common probe sequence can be designed to either eliminate or promote formation of secondary structures, either alone or in conjunction with the miRNA targets. Such secondary structures can be useful in reducing or increasing ligation efficiency as appropriate. Typical common probe sequences are provided in Table 1.

Discrimination Probe Design. The discrimination probes used with the methods of the present invention are commercially synthesized, HPLC or PAGE purified, DNA oligonucleotides. At least one discrimination probe is required for each miRNA being detected. In accordance with an embodiment, about 5-100 discrimination probes are used in each probe set. Each discrimination probe comprises a recognition sequence at its 5' end that is complimentary to the target miRNA of interest being detected, and also comprises a variable length coding sequence (VLCS) at the 3' end that can be used to identify the hybridized probe by its unique length. In one embodiment, the recognition sequence is exactly the same length as the microRNA target and entirely complementary to the microRNA sequence.

In some other embodiments, the recognition sequence may vary from full complementary, for example, in another embodiment, the length of the recognition sequence is shorter than the microRNA target while maintaining perfect complementarity. In another embodiment, the length of the recognition sequence is longer than the microRNA target while maintaining perfect complementarity and extending into the adapter sequence.

In accordance with an embodiment, the discrimination probes comprise a 5' recognition sequence having a DNA oligonucleotide sequence which has antisense complementarity to the specific miRNA of interest and having a 3' variable length coding sequence (VLCS) having at least 5 to about 200 nucleotides in length.

A VLCS on a discrimination probe, in one or more embodiments, can vary in length from 5-150 nt, however, in accordance with other embodiments; the lengths can be made longer or shorter to enable distinct identification. Longer discrimination probe sequences can be generated using known cloning techniques to create probes that are between 100-100,000 bp. The minimum length difference between VLCS tags is determined by the desired level of multiplexing and the sizing resolution and sizing dynamic range of the downstream size discrimination technique used to identify them. In embodiments using with detection platforms with single nucleotide resolution such as poly-acrylamide gel electrophoresis, capillary electrophoresis or, single molecule free solution hydrodynamic separation, VLCS tags are typically separated by 3-10 nucleotides. In embodiments using agarose gel electrophoresis, VLCS tags are typically separated by 10-100 nucleotides.

In accordance with an embodiment, the 3' terminus of the discrimination probe is blocked by -ddC to prevent unwanted ligation products. In alternative embodiments, other blocking moieties may also be used, for example, such as $NH_2$. In accordance with a further embodiment, the 3' terminus of the discrimination probe can be labeled with a detectable moiety, for example, such as Cy3, Cy5, Alexa488, Alexa647, FITC, etc.

In accordance with an embodiment, the 5' terminus of the discrimination probe is pre-adenylated so that ligation can be performed in the absence of ATP, reducing unwanted ligation products. Pre-adenylation can be performed using any known methods in the art, including enzymatically or chemically.

In accordance with another embodiment, the discrimination probe comprises alternative nucleic acid residues such as locked nucleic acids or peptide nucleic acids may be substituted at various positions to increase binding specificity.

It will be understood by those of ordinary skill in the art that each discrimination probe comprises 2 regions, a recognition sequence and a VLCS tag. In accordance with an embodiment, the recognition sequence is typically fully complementary to the target miRNA sequence of interest. In accordance with other embodiments, the recognition sequence may vary from having a fully complementary sequence to the target miRNA sequence of interest.

In accordance with some embodiments, the discrimination probe comprises a detectable internal label.

In accordance with an embodiment, the VLCS tag typically is comprised of sequences not found within the host genome to prevent unwanted hybridization to background RNA/DNA molecules. In one or more alternative embodiments, the discrimination probe sequences can be designed to either eliminate or promote formation of secondary structures, either alone or in conjunction with the miRNA targets. Such secondary structures can be useful in reducing or increasing ligation efficiency as appropriate. Examples of some discrimination probe sequences are provided in Table 1.

As used in the methods described herein, the target RNA of interest is analyzed and identified using size discrimination methods. Examples of size discrimination methods include, but are not limited to, gel electrophoresis, capillary electrophoresis and SML-FSHS.

Ligo-miR EZ methods. FIG. 1 shows a schematic of the overall Ligo-miR™ analysis methods of the present invention. In accordance with an embodiment, in the first ligation step, the method begins with obtaining about 0.1-5 µL of total RNA sample, and adding a sufficient quantity of adenylated adapter probe (50-1000 nM), ligase (50-500 units), ligase buffer (0.1-5 µL), and water. It will be understood by those of ordinary skill in the art that ligases that can be used in the methods of the present invention include, for example, T4 RNA Ligase 1, T4 RNA Ligase 2 truncated, T4 RNA Ligase 2 truncated KQ, T4 RNA Ligase 2 truncated K227Q, Thermostable 5' App DNA/RNA Ligase, etc. In certain embodiments, additives such as PEG (polyethylene glycol) (0-40%) and DMSO (Dimethyl sulfoxide) (0-30%) can also be added to increase ligation efficiency. The final reaction volume is about 10 µL. The mixture is then incubated at 25° C. for about 0.25 to 48 hours and is followed by a 65° C. heat denaturing step for about 1-60 minutes, preferably about 1, 2, 5, 10, 15, 20, 30 up to 60 minutes. In some embodiments, the incubation step can also be performed at lower temperatures such as 4° C. or higher temperatures such as 65° C. to reduce ligation bias and increase ligation efficiency.

In accordance with an embodiment, in the second ligation step, about 5 µL of the previous reaction mixture is obtained and a sufficient quantity of the common probe (10-1000 nM), discrimination probes (10-1000 nM), ligase (50-500 units), ligase buffer (0.1-5 µL), and water is added. It will be understood by those of ordinary skill, that in for the second step, ligases that can be used include, for example, T4 DNA Ligase, 9° N DNA Ligase, Ampligase, T4 RNA Ligase 2, E. Coli DNA Ligase, Taq Ligase, etc. In some embodiments, additives such as PEG (polyethylene glycol) (0-40%) and DMSO (Dimethyl sulfoxide) (0-30%) can also be added to increase ligation efficiency. The final reaction volume is about 10 µL. The reaction is then subjected to thermal cycling between 95° C. (0.5-5 minutes hold) and 45° C. (1-100 minutes hold) for 1-100 cycles depending on how much amplification is required.

Figure 2:
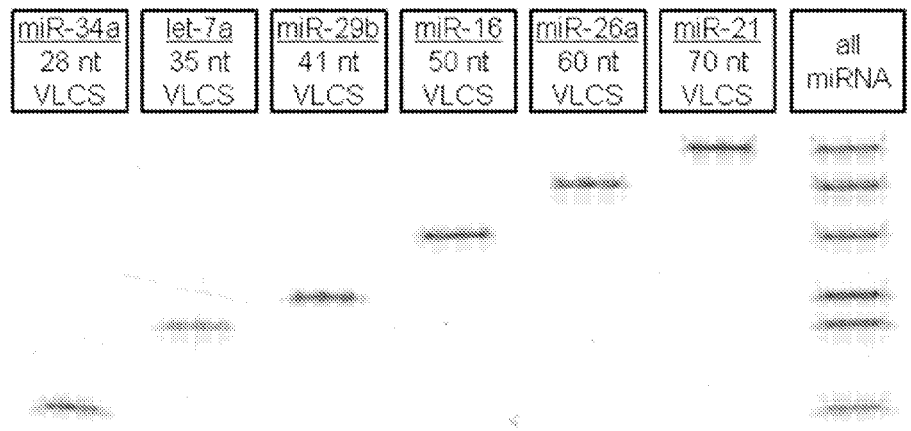
FIG. 2 shows a gel using the PCR-free, 6-plex Ligo-miR™ assay of the present invention to perform multiplex detection of let-7a, miR-16, miR-21, miR-26a, miR-29b, and miR-34a using a single reaction. The respective length encoded ligation products are only formed when the correct miRNA target is present, enabling identification by size. No cross-talk is seen between the probe sets.
Figure 3:
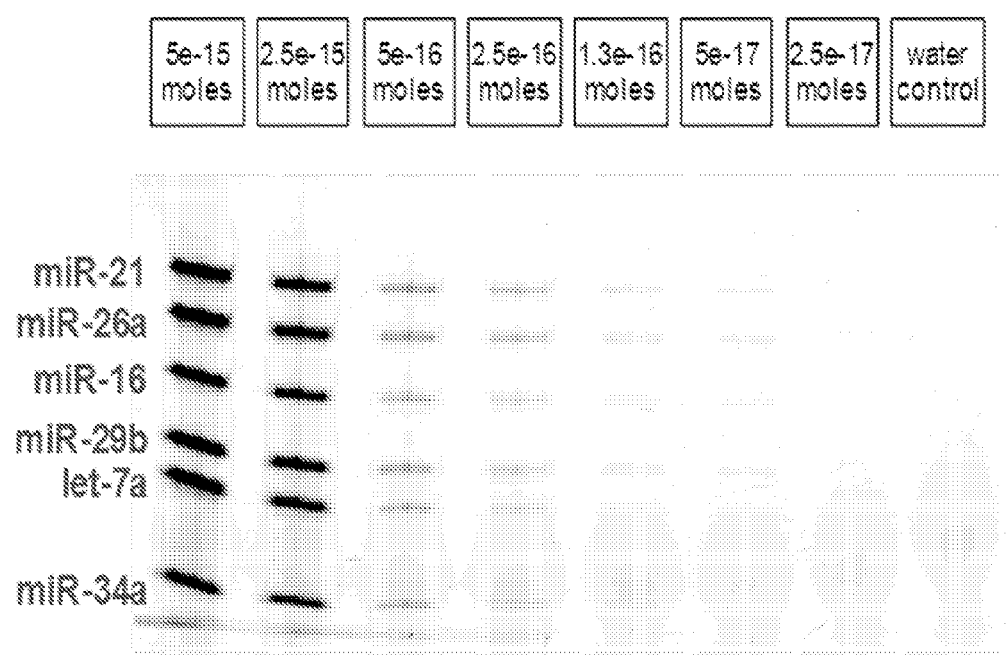
FIG. 3 shows a typical gel image of 6-plex analysis of titrated miRNA where all 6 miRNA targets are serially diluted simultaneously.
Figure 4:
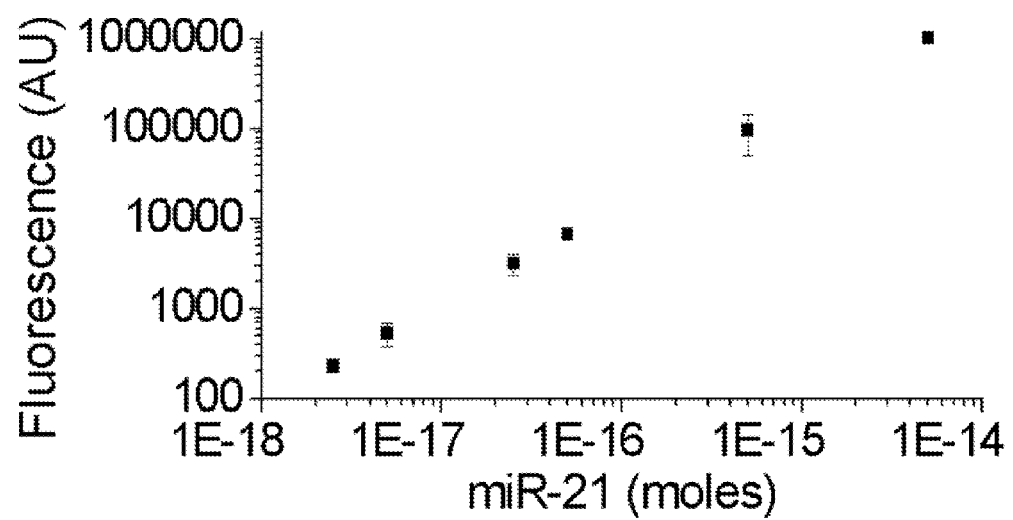
FIG. 4 depicts a titration curve of miR-21 obtained using Ligo-miR EZ. High sensitivity ($<2.5 \times 10^{-18}$ moles), excellent linearity, and high repeatability are achieved. Shown are the average and standard deviation from 3 independent experiments. The microfluidic Ligo-miR HD will enable even higher yoctomole level sensitivity ($10^{-23}$ moles).

After thermocycling, in accordance with an embodiment, the sample is then subjected to PAGE (poly-acrylamide gel electrophoresis) to separate the hybridized products. Typically, 5 µL of the sample is mixed with gel loading buffer and analyzed on a denaturing 15% TBE-urea polyacrylamide gel for about 50 minutes at 300V, enabling separation of the microRNA reaction products. In an alternative embodiment, agarose gel electrophoresis can also be used to separate the hybridized products. The separated gel products are imaged on a Typhoon Variable Mode Imager (GE). A typical gel image is provided in FIG. 2. FIG. 3 shows a typical gel image of 6-plex analysis of titrated miRNA targets. In alternative embodiments, CCD-based or film based imagers can also be used to obtain a gel image. Image analysis is used to identify the microRNA expression levels based on gel band position and integrated band intensity. FIG. 4 shows a typical titration curve obtained from the image analysis of miR-21 using FIG. 3.

In accordance with another embodiment, the thermocycled samples can be analyzed using capillary electrophoresis instead of slab gel electrophoresis. The resultant electropherogram can then be analyzed for to obtain microRNA expression levels based on peak position and integrated peak intensity.

TABLE 1

Sequences of Adapter, Common, and Discrimination Probes

| Probe Name | Length | 5' Mod | 3' Mod | Sequence 5'->3' |
|---|---|---|---|---|
| rA-1 adapter probe | 18 | phos | ddC | 5'-/5Phos/rAC TGT AGG CAC CAT CAA T/3ddC/-3' (SEQ ID NO: 1) |
| rA-2 adapter probe | 18 | phos | Biotin-TEG | 5'-/5Phos/rAC TGT AGG CAC CAT CAA TC/3BiotinTEG/-3' (SEQ ID NO: 2) |
| rA-3 adapter probe | 19 | phos | Cy5 | 5'-/5Phos/rAC TGT AGG CAC CAT CAA TC/3Cy5Sp/-3' (SEQ ID NO: 3) |
| rG adapter probe | 19 | phos | Cy5 | 5'-/5Phos/rGC TGT AGG CAC CAT CAA TC/3Cy5Sp/-3' (SEQ ID NO: 4) |
| rU adapter probe | 19 | phos | Cy5 | 5'-/5Phos/rUC TGT AGG CAC CAT CAA TC/3Cy5Sp/-3' (SEQ ID NO: 5) |
| rC adapter probe | 19 | phos | Cy5 | 5'-/5Phos/rCC TGT AGG CAC CAT CAA TC/3Cy5Sp/-3' (SEQ ID NO: 6) |
| dA-1 adapter probe | 19 | phos | ddC | 5'-/5Phos/AC TGT AGG CAC CAT CAA TC/3ddC/-3' (SEQ ID NO: 7) |
| dA-2 adapter probe | 19 | phos | Cy5 | 5'-/5Phos/AC TGT AGG CAC CAT CAA TC/3Cy5Sp/-3' (SEQ ID NO: 8) |
| dG adapter probe | 19 | phos | Cy5 | 5'-/5Phos/GC TGT AGG CAC CAT CAA TC/3Cy5Sp/-3' (SEQ ID NO: 9) |
| dT adapter probe | 19 | phos | Cy5 | 5'-/5Phos/TC TGT AGG CAC CAT CAA TC/3Cy5Sp/-3' (SEQ ID NO: 10) |
| dC adapter probe | 19 | phos | Cy5 | 5'-/5Phos/CC TGT AGG CAC CAT CAA TC/3Cy5Sp/-3' (SEQ ID NO: 11) |
| Common probe | 19 | Cy5 | — | 5'-/5Cy5/GA TTG ATG GTG CCT ACA GT-3' (SEQ ID NO: 12) |
| miR-34a discrimination probe | 50 | phos | — | 5'-/5Phos/AC AAC CAG CTA AGA CAC TGC CAA TCC TGT TAC CAT CGT AGG CAC CTG AAA-3' (SEQ ID NO: 13) |
| let-7a discrimination probe | 57 | phos | FAM | 5'-/5Phos/AA CTA TAC AAC CTA CTA CCT CAA TCC TGT TAC CAG TGG CTG CTG CCA GTG GCG ATA A/36-FAM/-3' (SEQ ID NO: 14) |
| miR-29b discrimination probe | 64 | phos | — | 5'-/5Phos/AA CAC TGA TTT CAA ATG GTG CTA ATC CTG TTA CCA GTG GCT GCT GCC ATC GTA GGC ACC TGA AA -3' (SEQ ID NO: 15) |
| miR-16 discrimination probe | 72 | phos | — | 5'-/5Phos/CG CCA ATA TTT ACG TGC TGC TAA TCC TGT TAC CAG TGG CTG CTG CCA GTG GCG ATA AGT CGT GTC TTA CCG G -3' (SEQ ID NO: 16) |
| miR-26a discrimination probe | 82 | phos | — | 5'-/5Phos/AG CCT ATC CTG GAT TAC TTG AAA TCC TGT TAC CAG TGG CTG CTG CCA GTG GCG ATA AGT CGT GTC ATC GTA GGC ACC TGA AA-3' (SEQ ID NO: 17) |
| miR-21 discrimination probe | 92 | phos | — | 5'-/5Phos/TC AAC ATC AGT CTG ATA AGC TAA TCC TGT TAC CAG TGG CTG CTG CCA GTG GCG ATA AGT CGT GTC TTA CCG GGT TGG ACT CAA GAC GAT AGT-3' (SEQ ID NO: 18) |

Ligo-miR HD Methods. For the HD methods of the present invention, in an embodiment, the first and second ligation reactions proceed as detailed above for Ligo-miR™ EZ embodiments.

Separation and analysis of the hybridized products is performed using single molecule free solution hydrodynamic separation (SML-FSHS). In an embodiment, SML-FSHS is performed using a PicoSep instrument (Circulomics) fitted with a 2 µm inner diameter, 75 cm long fused silica microcapillary at 100 psi with TE buffer as the loading and elution buffer. In an alternative embodiment, a 1 µm inner diameter microcapillary can be used for higher sizing resolution. In certain other embodiments, denaturing buffer conditions can also be used.

Figure 5:
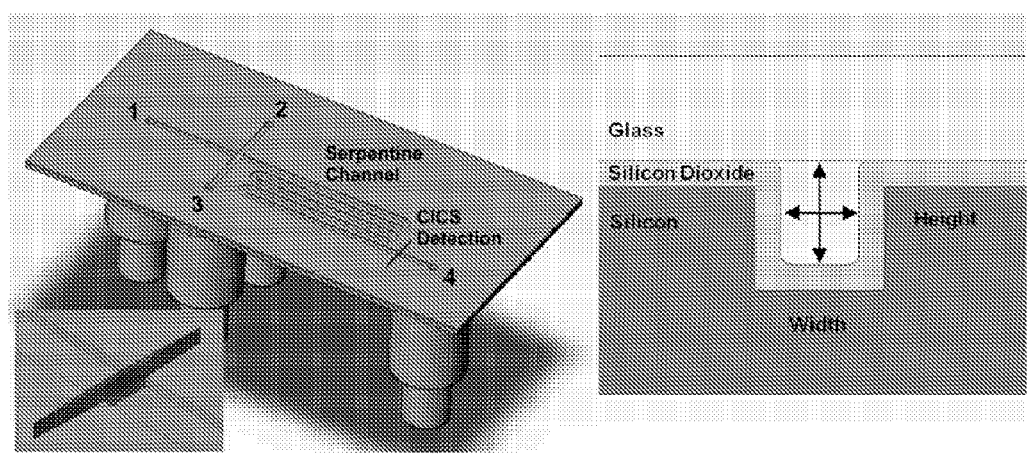
FIG. 5 depicts an illustration of a SML-FSHS microfluidic device used for Ligo-miR HD analysis which is fabricated from anodic bonding of silicon to glass. Separation is performed in the buffer-filled serpentine separation channel after which cylindrical illumination confocal spectroscopy (CICS) based single molecule detection is used to analyze the separated peaks. The CICS laser sheet spans the entire channel cross-section for 100% mass detection efficiency (inset). The dimensions of the channels are controlled by balancing silicon etch depth with the thickness of the silicon dioxide (right).

In accordance with yet another embodiment, a microfluidic device can be used instead of a microcapillary to perform SML-FSHS analysis. A schematic illustration of SML-FSHS microfluidic device is shown in FIG. 5. The device contains a serpentine shaped microfluidic channel with width and depth of 1 µm and length of 1 m.

Figure 6:
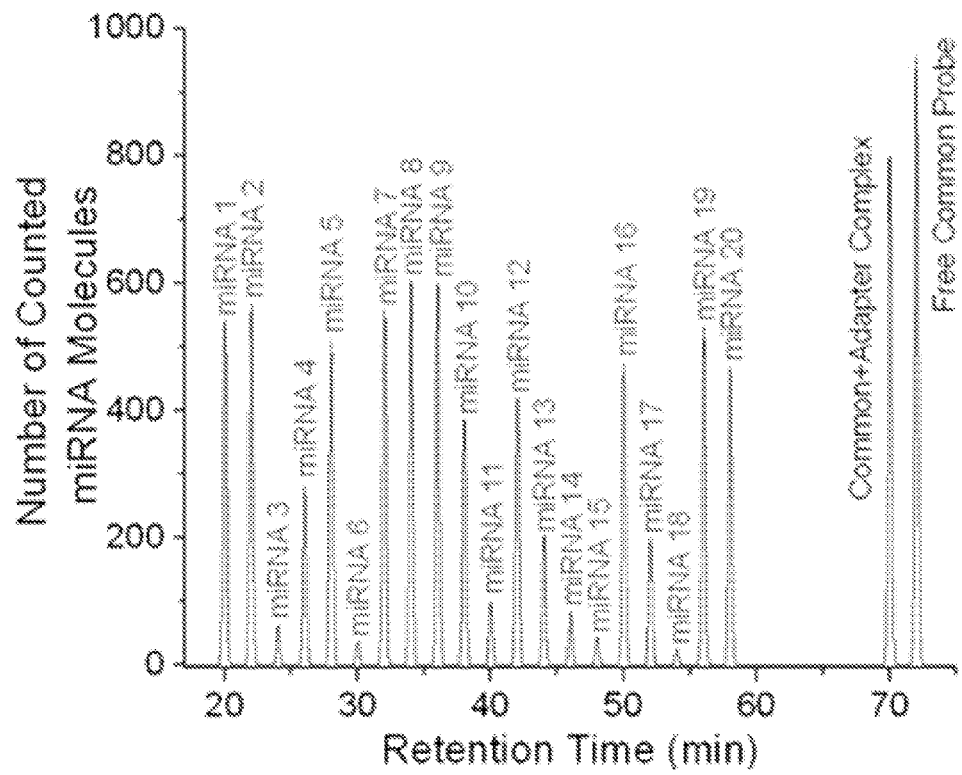
FIG. 6 depicts a typical chromatogram of 20-plex miRNA analysis performed using Ligo-miR HD. SML-FSHS is used to identify the Ligo-miR™ products by size and quantify them by single molecule counting. Each Ligo-miR™ product is identified as a size specific peak based on the length of its variable length coding sequence. Quantity is determined by single molecule counting of the Alexa-647 labels.

The resultant SML-FSHS chromatogram can then be analyzed for to obtain microRNA expression levels based on peak position, which is correlated to size, and single molecule counts, which is correlated to amount. A representative chromatogram is provided in FIG. 6.

Figure 7:
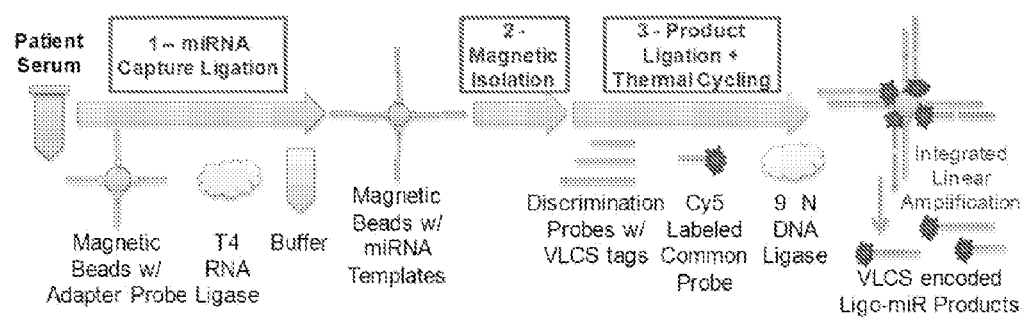
FIG. 7 shows a schematic of the Ligo-miR Bead embodiment of the present invention. This embodiment uses magnetic beads and a 2-step ligation to integrate miRNA capture and multiplex detection into a single streamlined process. The first ligation captures miRNA from serum and forms miRNA templates concentrated on the bead surface. A magnetic isolation removes all background impurities. The second ligation includes a 50-fold linear amplification and generates single stranded miRNA specific ligation products which are identified and quantified by single molecule analysis.

Ligo-miR Bead Methods. FIG. 7 shows a schematic of an embodiment of the overall method of the present invention. Adapter probes are coupled to magnetic beads by conjugating 3'-biotin labeled adapter probes with streptavidin coated magnetic beads using standard streptavidin-biotin binding chemistry known in the art. For the first ligation step, about 1.5 µL of raw sample are obtained and adapter probe coupled magnetic beads are added, along with a sufficient quantity of ligase, ligase buffer, and water. Raw samples can include blood, serum, cell lysate, etc. It will be understood by those of ordinary skill that ligases that can be used in the inventive methods include, for example, T4 RNA Ligase 1, T4 RNA Ligase 2 truncated, T4 RNA Ligase 2 truncated KQ, T4 RNA Ligase 2 truncated K227Q, Thermostable 5' App DNA/RNA Ligase, etc. In some embodiments, additives such as PEG (polyethylene glycol) and DMSO (Dimethyl sulfoxide) can also be added to increase ligation efficiency. The final reaction volume is about 10 µL. Incubate at 25° C. for about 1 to 4 hours, followed by a 65° C. heat denaturing step for about 20 minutes. In alternative embodiments, incubation of the solution can also be done at lower temperatures such as 4° C. or higher temperatures such as 65° C. to reduce ligation bias and increase ligation efficiency. In accordance with one or more embodiments, the present method ligates the 3'-OH present on every miRNA to the 5'-App on the adapter probe-coupled beads to create miRNA templates tethered to the bead surface.

The beads are then magnetically isolated, washed and resuspended in buffer. For the second ligation step, about 5 µL of the resuspended bead mixture are obtained and add the common probe, discrimination probes, ligase, ligase buffer, and water. As in other embodiments discussed above, ligases that can be used in the inventive methods include T4 DNA Ligase, 9° N DNA Ligase, Ampligase, T4 RNA Ligase 2, E Coli DNA Ligase, Taq Ligase, etc. In alternative embodiments, additives such as PEG (polyethylene glycol) and DMSO (Dimethyl sulfoxide) can also be added to increase ligation efficiency. The final reaction volume is about 10 µL.

The above products are then thermal cycled between 95° C. (0.5-5 minutes hold) and 45° C. (1-100 minutes hold) for 1-100 cycles depending on how much amplification is required.

The isolated samples are then separated using PAGE. In accordance with one or more embodiments, about, 5 µL of the sample is mixed with gel loading buffer and analyzed on a denaturing 15% TBE-urea polyacrylamide gel for 50 minutes at 300V, enabling separation of the microRNA reaction products. Alternatively, in some embodiments, agarose gel electrophoresis can also be used. The separated gel is imaged on a Typhoon Variable Mode Imager (GE). Alternatively, depending on the detectable moiety used, CCD-based or film based imagers can also be used to obtain a gel image. Image analysis is used to identify the microRNA expression levels based on gel band position and integrated band intensity.

In accordance with another embodiment, the sample can also be analyzed using capillary electrophoresis, or in some embodiments the sample can be analyzed using SML-FSHS.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method for detection of one or more target miRNA of interest in a sample comprising:
   a) obtaining a sample containing one or more target miRNA of interest;
   b) adding to the sample of a) a sufficient amount of adapter probes and a sufficient amount of a first ligase
   c) performing a first ligation step by incubation and allowing the adapter probes to be ligated to the 3'-OH ends of the one or more target miRNA of interest in the sample;
   d) adding to the sample of b) a sufficient amount of common probes and discrimination probes, and a sufficient amount of a second ligase;
   e) performing a second ligation step by incubating the sample of c) for a sufficient amount of time to effect hybridization of the common probes and discrimination probes of d) with ligated one or more target miRNA of interest and adapter probes of b) and to allow ligation between the discrimination probes and common probes; and f) analysis of the hybridized and ligated common probes and discrimination probes of d) with the ligated one or more target miRNA of interest and adapter probes of b) by one or more size discrimination methods.

2. The method of claim 1, wherein the adapter probe comprises 5-50 DNA nucleotides in length and is phosphorylated at the 5' end.

3. The method of claim 2, wherein the adapter probe is pre-adenylated at the 5' end.

4. The method of claim 3, wherein the adapter probe is blocked at the 3' end with ddC or $NH_2$.

5. The method of claim 1, wherein the discrimination probes comprise a 5' recognition sequence having a DNA oligonucleotide sequence complementary to the one or more target miRNA of interest and having a 3' variable length coding sequence (VLCS) having at least 5 to about 200 nucleotides in length.

6. The method of claim 5, wherein the VLCS length is specific to one or more target miRNAs of interest.

7. The method of claim 1, wherein the common probe comprises a detectable label which is selected from the group consisting of fluorescent probes, near infra-red probes, FRET probes, luminescent probes and radionuclides.

8. The method of claim 1, wherein in f) the size discrimination is performed using electrophoresis.

9. The method of claim 1, wherein in f) the size discrimination is performed using single molecule free solution hydrodynamic separation (SML-FSHS).

10. The method of claim 1, wherein in f) the size discrimination is performed using chromatography.

11. The method of claim 1, wherein the incubation step e further comprises thermocycling the sample for 1-100 cycles by heating the sample for about 0.25 minutes to about 5 minutes at 45° C. to about 95° C. for denaturation and hybridization of the discrimination and common probes, followed by heating the sample for about 0.25 minutes to about 100 minutes at 4° C. to about 80° C. to complete ligation of the discrimination and common probes.

12. The method of claim 1, wherein internal controls are added to account for variations in ligation efficiency.

13. The method of claim 1, wherein the first ligase is selected from the group consisting of T4 RNA ligase 1, T4 RNA ligase 2 truncated, T4 RNA ligase 2 K227Q, T4 RNA ligase 2 truncated KQ, and *Methanobacterium thermoautotrophicum* RNA ligase.

14. The method of claim 1, wherein the second ligase is selected from the group consisting of *E. Coli* DNA ligase, Taq DNA ligase, 9° N DNA ligase, T4 DNA ligase, T4 RNA ligase 2, and Ampligase.

15. The method of claim 1, wherein the method further comprises PCR amplification of the reaction products comprising the hybridized and ligated common probes and discrimination probes of d) with the ligated one or more target miRNA of interest and adapter probes of b), is performed after the second ligation step but before size discrimination methods.

* * * * *